US 6,489,097 B2

(12) United States Patent
Hirose et al.

(10) Patent No.: US 6,489,097 B2
(45) Date of Patent: *Dec. 3, 2002

(54) METHOD FOR THE DETECTION OF TELOMERASE ACTIVITY

(75) Inventors: Minoru Hirose; Junko Hashimoto; Tadashi Yoshimura, all of Tokyo (JP)

(73) Assignee: Chugai Seiyaku Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/202,972

(22) PCT Filed: Jun. 27, 1997

(86) PCT No.: PCT/JP97/02251

§ 371 (c)(1),
(2), (4) Date: Dec. 23, 1998

(87) PCT Pub. No.: WO98/00563

PCT Pub. Date: Jan. 8, 1998

(65) Prior Publication Data

US 2002/0025518 A1 Feb. 28, 2002

(30) Foreign Application Priority Data

Jun. 28, 1996 (JP) .............................. 8-169920

(51) Int. Cl.[7] .......................... C12Q 1/68; C12P 19/34; C07H 21/04; C07H 21/00
(52) U.S. Cl. .................... 435/6; 435/91.2; 435/91.52; 536/24.33; 536/24.3; 536/25.32
(58) Field of Search .................. 435/6, 91.2, 91.52; 536/24.3, 25.32

(56) References Cited

U.S. PATENT DOCUMENTS

| 5,629,154 A | 5/1997 | Kim et al. ............... 435/6 |
| 5,648,215 A | * 7/1997 | West et al. ............. 435/6 |
| 5,804,380 A | * 9/1998 | Harley et al. .......... 435/6 |

FOREIGN PATENT DOCUMENTS

| CA | 2020958 | 1/1991 | .......... C07H/21/00 |
| WO | 8902476 | 3/1989 | .......... C12Q/1/68 |
| WO | 9101384 | 2/1991 | .......... C12Q/1/68 |
| WO | 9513381 | 5/1995 | .......... C12N/15/54 |

OTHER PUBLICATIONS

Ohyashiki, J.H., et al., *Non-radioisotopic and Semi-quantitative Procedure for Terminal Repeat Amplification Protocol,* Jpn. J. Cancer Res., vol. 87, pp. 329–331 (1996).

Kim, N.W., et al., *Specific Association of Human Telomerase Activity with Immortal Cells and Cancer,* Science, vol. 266, pp. 2011–2015 (1994).

Piatyszek, M. A.., et al., *Detection of Telomerase Activity in Human Cells and Tumors by a Telomeric Repeat Amplification* Protocol (TRAP), Methods in Cell Science, vol. 17, pp. 1–15 (1995).

* cited by examiner

Primary Examiner—Stephanie Zitomer
Assistant Examiner—Joyce Tung
(74) Attorney, Agent, or Firm—Davidson, Davidson & Kappel, LLC

(57) ABSTRACT

A method for the detection of telomerase activity, for the detection of cancer cells and for the diagnosis of cancer comprising amplifying an oligonucleotide sequence extended by a DNA extension reaction with a telomerase and hybridizing the resulting amplified product with a probe labelled with a non-radioactive material to detect the telomerase activity, as well as a diagnositic kit for use in said method for the detection and diagnosis.

3 Claims, 13 Drawing Sheets

A: TRAP product of K562 (equivalent to 1000 cells)
B: TRAP product of K562 (equivalent to 100 cells)
C: TRAP product of MKN1 (equivalent to 1000 cells)
D: TRAP product of MKN1 (equivalent to 100 cells)

METHOD FOR THE DETECTION OF TELOMERASE ACTIVITY

This application is a 371 of PCT/JP97/02251, filed Jun. 27, 1997.

TECHNICAL FIELD

The present invention relates to a method for the detection of telomerase activity, a method for the detection of cancer cells, a method for the diagnosis of cancer, as well as a kit for the detection of cancer cells and/or the diagnosis of cancer.

BACKGROUND ART

Human somatic cells have 22 pairs of autosomes and a pair of sex chromosomes. A total of 46 chromosomes are present in a cell. These chromosomes are independent of each other and rarely associated with each other. Telomeres are responsible for this important function and telomerase plays a role in maintaining the presence of telomeres. Telomeres are located in the terminal end of chromosomes and, in human, have a characteristic sequence of a few hundreds of repeated 6 bases 5'-TTAGGG-3'. The replication of DNA is essential to proliferation of cells by division and, based on the mechanism of the DNA replication, the terminal telomere of a chromosome is shortened once DNA has been replicated. Whenever the cell division is repeated, the telomeric sequence is shortened. Deletion of this portion induces association of chromosomes which causes adverse effects on cells. Further, other gene abnormalities may also occur and cells are led to death (senescence and death of cells). Telomeric sequences have an important role in the senescence and death of cells, that is, alternation of generations of cells. However, it is considered that if telomeric sequences of some cell populations which should naturally die (aged cell populations in which gene abnormalities have been accumulated) are still continuously added by the action of telomerase, a part of the populations may be immortalized and eventually cancerized. Accordingly, the detection of telomerase activity is very useful in the diagnosis of cancer or in monitoring the prognosis of treatment.

Recently, TRAP (telomeric repeat amplification protocol) for detecting the telomerase activity with a high sensitivity by using PCR (polymerase chain reaction) has been developed: Kim N. W. et al., (1994) Science, 206, 2011–2015; Piatyszek M. A. et al., (1995) Meth. Cell Sci., 17, 1–15. This method involves the detection of telomerase by a single primer extension assay system and is roughly divided in three steps. First, telomerase is extracted from cells. Then, extension reaction of TTAGGG chain by the telomerase is carried out and the reaction products are amplified by PCR using two primers, called TS and CX primers. Finally, the amplified products are electrophoresed to detect the telomerase activity by confirming ladders in autoradiography. This method has improved the detection sensitivity, enabling the detection of telomerase activity even in a small number of cells, such as 10 cells.

Among the above three steps, however, the detection system must involve electrophoresis, which requires complicated operations and a long period of time. For example, analysis of $^{32}P$- or fluorescence-labelled reaction products by polyacrylamide gel electrophoresis, HPLC, or other means is still required, so that the number of samples to be detected is limited and, in the case of $^{32}P$, its handling, such as treatment of gel or a large amount of waste liquid, is not easy. In addition, it will take a long time to conduct a series of operations, such as preparation of gel, electrophoretic separation (analysis) and exposure (detection), usually 2 to 48 hours.

These problems are very inconvenient, especially in the diagnosis of progression and prognosis of cancer which requires real time analysis, and it is also difficult to analyse a large amount of samples. Thus, there is a need for the development of another detection system which may replace the electrophoresis or autoradiography.

DISCLOSURE OF INVENTION

It is an object of the present invention to provide a method enabling rapid detection of telomerase activity with a high sensitivity.

The present inventors have eagerly studied the above problems and, as a result, found that telomerase activity can be rapidly detected with a high sensitivity by constructing a system comprising the DNA extension reaction with a teromerase in combination with the hybridization protection assay (HPA) developed by Gen-Probe, leading to the completion of the present invention.

That is to say, the present invention is a method for the detection of telomerase activity comprising amplifying an oligonucleotide sequence extended by a DNA extension reaction with a telomerase and hybridizing the resulting amplified product with a probe labelled with a non-radioactive labelling material to detect the telomerase activity. The non-radioactive labelling material includes, for example, acridinium esters, luminol, isoluminol, pyrogallol, protohemin, aminobutylethyl-n-isoluminol, aminohexylethyl-n-ethyl-isoluminol, and acridine derivatives.

The acridine derivatives may include, for example, those represented by the following formula I:

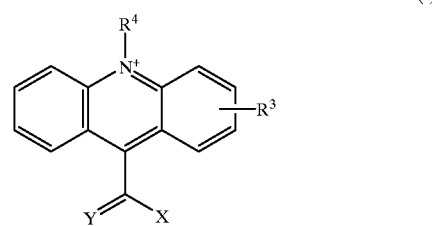

(I)

wherein X denotes a halogen, or a group represented by the following formula II:

(II)

in which $X^1$ is a nitrogen, phosphorus, boron or arsenic atom, $R^1$ is an alkoxy or aryloxy group, or a substituted or unsubstituted alkyl, alkenyl or aryl group, and $R^2$ is a hydrogen atom, or, an alkoxy or aryloxy group, or a substituted or unsubstituted alkyl, alkenyl or aryl group, or the following formula III:

(III)

in which $X^2$ is an oxygen or sulfur atom and $R^2$ is as defined above, Y denotes an oxygen or sulfur atom, or NH, $R^3$ denotes a hydrogen atom, an amino, hydroxy, thiol, carboxylic acid, halogen, nitro, alkoxy or aryloxy group, or a substituted or unsubstituted acetyl, alkyl, alkenyl or aryl group, $R^4$ denotes a substituted or unsubstituted alkyl, alkenyl or aryl group, and at least one of $R^1$, $R^2$, $R^3$ and $R^4$ comprises a reactive site capable of chemical bonding. The reactive site capable of chemical bonding herein means a site which binds to a probe. For example, when the bonding is effected through a linker and an amino linker having an amino group at the end thereof, said reactive site is a site which binds to the amino group. The substance capable of binding to this site includes, for example, a carboxylic acid derivative, preferably an acid halide or ester.

However, the present invention is not limited to the non-radioactive labelling materials described above. In addition to the acridine derivatives represented by the above formula I, those represented by the chemical formula I as shown in Japanese Patent No. 2602315 are also encompassed.

The oligonucleotide sequence extended through DNA extension reaction by a telomerase is amplified by a polymerase chain reaction using an oligonucleotide primer comprising at least a base sequence represented by "AGNGTT" wherein N is A, T, G or C at the 3' side and/or an oligonucleotide primer comprising the base sequence represented by SEQ ID NO: 21. This amplification may also be effected by RNA synthetic reaction using an oligonucleotide primer comprising at least a base sequence represented by "AGNGTT" wherein N is A, T, G or C at the 3' side and/or an oligonucleotide primer comprising the base sequence represented by SEQ ID NO: 21. A promoter sequence is added to at least one of oligonucleotide primers used in the RNA synthetic reaction.

Further, the amplification may also be carried out by polymerase chain reaction or RNA synthetic reaction using an oligonucleotide primer having any sequence which does not hybridize with the sequence represented by "TTAGGG" and has been added to the 5' side of either an oligonucleotide primer comprising the base sequence represented by SEQ ID NO: 21 or an oligonucleotide primer comprising a base sequence having at least one nucleotide deleted, substituted or added in the base sequence of said primer.

In the present invention, the conditions under which no hybridization occurs may include, for example, 30 to 120° C., preferably 37 to 90° C.

The oligonucleotide primer comprising at least a base sequence represented by "AGNGTT" wherein N is A, T, G or C at the 3' side includes that represented by SEQ ID NO: 1, and the oligonucleotide primer comprising the base sequence represented by SEQ ID NO: 21 includes that represented by SEQ ID NO: 2. Further, the promoter may include T7, T3 and SP6 RNA polymerase promoters.

Further, the present invention is a method for the detection of cancer cells comprising detecting the telomerase activity in the cancer cells by said method for the detection of the telomerase activity.

The cancer cells may include those contained in specimens obtained invasively or non-invasively. Specimens obtained invasively may include urinary bladder tissues, prostate gland tissues, uterus tissues, uterocervix tissues, udder tissues, pancreas tissues, liver tissues, large intestine tissues, stomach tissues, lung tissues, peripheral blood cells, kidney tissues, skin tissues, esophagus tissues, brain tissues and oral cavity tissues. Specimens obtained non-invasively may include urine, prostate gland juice, urinary bladder wash, uterus smear, pancreatic juice, duodenum juice, feces, oral cavity wash, enteron wash, saliva and sputum.

Further, the present invention is a method for the diagnosis of cancer comprising detecting cancer cells by said method for the detection of the cancer cells. The cancers include urinary bladder cancer, prostate gland cancer, uterus cancer, uterocervix cancer, breast cancer, pancreatic cancer, liver cancer, large intestine cancer, gastric cancer, lung cancer, kidney cancer, skin cancer, oral cavity cancer, esophagus cancer, brain tumor and leukemia.

Moreover, the present invention is a diagnostic kit comprising an oligonucleotide primer comprising at least a base sequence represented by "AGNGTT" wherein N is A, T, G or C at the 3' end, an oligonucleotide primer comprising the base sequence represented by SEQ ID NO: 21 or an oligonucleotide primer comprising a base sequence having at least one nucleotide deleted, substituted or added in the base sequence of the primer, and a probe labelled with a non-radioactive labelling substance. Said kit also comprises a promoter added to at least one primer. Examples of the promoter are as above listed. Said diagnostic kit further comprises an oligonucleotide primer having any sequence which does not hybridize with the sequence represented by "TTAGGG" and has been added to the 5' side of either an oligonucleotide primer comprising the base sequence represented by SEQ ID NO: 21 or an oligonucleotide primer comprising a base sequence having at least one nucleotide deleted, substituted or added in the base sequence of said primer.

Said diagnostic kit is used in the detection of telomerase activity or the diagnosis of cancer. Cancers to be diagnosed include urinary bladder cancer, prostate gland cancer, uterus cancer, uterocervix cancer, breast cancer, pancreatic cancer, liver cancer, large intestine cancer, gastric cancer, lung cancer, kidney cancer, skin cancer, oral cavity cancer, esophagus cancer, brain tumor and leukemia.

Further, the present invention is a method for the detection of telomerase activity comprising amplifying an oligonucleotide sequence extended through DNA extension reaction by a telomerase and detecting the resulting amplified product without using a radioactive labelling substance.

Hereinafter the present invention will be described in detail.

The present invention is a method for the detection of telomerase activity in cells or cell extracts (hereinafter referred to "cell extracts"). The present invention is to detect the telomerase activity using as a measure or index the presence or absence of an oligonucleotide sequence which is extended by the DNA extension reaction by a telomerase, and characterized in said oligonucleotide sequence is amplified and the amplified product is hybridized with a probe labelled with a non-radioactive labelling substance.

(1) Preparation of Cell Extracts and Amplification of Telomeric Repeat Sequences First, cell extracts containing a telomerase are prepared from a cancer tissue or cell line.

The kind of cancer tissues or cell lines is not particularly limited but includes cancer tissues such as large intestine and liver cancers, as well as cancer cell lines of large intestine cancer, liver cancer, uterocervix cancer, chronic myelogenous leukemia, glioblastoma, breast cancer, fibrosarcoma or the like, for example, K562, MKN1, HeLa, U937, U373MG, T98G, A172, MCF-7, HT-1080, LoVo, WiDr, SW857 and VA-4.

The cell extraction may be carried out by any known method with or without some modifications: Kim N. W. et al., (1994) Science, 206, 2011–2015.

Then, an oligonucleotide primer comprising at least a base sequence "AGNGTT" wherein N is A, T, G or C at the 3' side, hereinafter sometimes referred to as "primer 1", (for example, SEQ ID NO: 1) is added to the cell extract and the extension reaction of DNA is carried out. Preferably, the base sequence "AGNGTT" is desinged and synthesized such that it is 3' terminal end of said primer 1. The length of said primer 1 is not particularly limited and the primer may be arbitrarily designed so long as at least base sequence "AGAGTT", "AGTGTT", "AGGGTT" or "AGCGTT" is contained at the 3' side. For example, the length of the sequence is preferably 6 to 100 bases, more preferably 11 to 60 bases.

The DNA extended by the telomerase extension reaction (telomeric repeat sequence) is then amplified. The telomeric repeat sequence may be amplified by, for example, the polymerase chain reaction or RNA synthesis method. By using the polymerase chain reaction or RNA synthesis method, detection results may be obtained with a high sensitivity.

When the polymerase chain reaction is carried out, said primer 1 and/or, eg., an oligonucleotide primer comprising the base sequence represented by SEQ ID NO: 21, hereinafter also referred to as "primer 2" (for example, SEQ ID NO: 2) is used as a primer. These primers may be chemically synthesized using a commercially available DNA synthesizer.

The polymerase chain reaction is carried out in a conventional assay buffer. A desired DNA may be obtained in a large amount by the polymerase chain reaction.

When the telomeric repeat sequence is amplified using the RNA synthesis method, the amplification may be carried out by, for example, the known procedures called TMA (Transcription Mediated Amplification) method (Japanese Patent Application Laying Open No. 4-500759).

Preferably, said TMA method is modified when used to amplify the sequence. Thus, a promoter sequence (hereinafter referred to as "promoter") is added to the 5' end of the primer 1 as shown in FIG. 1 and DNA extension reaction is carried out using a telomerase as shown in FIG. 1 (1). The promoter may include, for example, T7 polymerase promoter such as SEQ ID NOs: 13 to 19, T3 polymerase promoter such as SEQ ID NO: 20, and SP6 polymerase promoter. However, the present invention is not limited to the promoters represented by said SEQ ID NOs.

Then, a reverse primer is used to convert the DNA into a double strand as shown in FIG. 1 (2). The reverse primer used herein is an oligonucleotide primer used to convert the .single stranded DNA extended by a telomerase into a double strand. As the reverse primer, for example, said primer 2 may be used.

From the double stranded DNA, a polymerase corresponding to said promoter is used to synthesize an RNA. For example, when T7 polymerase promoter, T3 polymerase promoter or SP6 polymerase promoter is used, T7 RNA polymerase, T3 RNA polymerase or SP6 RNA polymerase, respectively, is used to synthesize the RNA: FIG. 1 (3).

In the present invention, however, either one or both of the primers 1 and 2 may be used to carry out the RNA synthesis reaction. When either one of said primers is used, a promoter is added to the 5' end of said primer to carry out the RNA synthesis reaction. When both of said primers are used, a promoter(s) may be added to the 5' end(s) of the either one or both of said primers to carry out the RNA synthesis reaction.

The resulting RNA is subjected to DNA extension reaction using a reverse primer such as primer 2 to form a hybrid of DNA and RNA as shown in FIG. 1 (4). The RNA is decomposed and the DNA is extended to yield a double stranded DNA. This double stranded DNA fragment is used as a template to synthesize RNA using the above described various polymerases as shown in FIG. 1 (6). These reactions as shown in FIG. 1 (3) to (6) are repeated to symthesize in a large amount (amplify) the RNA. To stop the reaction, the reaction mixture is heated to, for example, $_{60}°$ C. In these procedures, the desired RNA may be obtained in a large amount.

Alternatively, instead of the reverse primer used in said modified TMA method, an oligonucleotide obtained by adding any sequence, that is, a base sequence randomly selected and synthesized so that it does not hybridize to the base sequence represented by "TTAGGG", to the 5' end of said reverse primer, may be used: refer to FIG. 1 (2). In the present invention, the oligonucleotide sequence randomly selected and synthesized is referred to as a tag sequence and a reverse primer to which a tag sequence is linked is referred to as a tag-sequence reverse primer. The tag sequence may also be linked to the full length reverse primer or a primer having a part (1 to 8 bases, preferably 4 to 6 bases) deleted, substituted or added in the 5' or 3' end of the reverse primer. Further, the tag sequence should be synthesized so that it does not hybridize to the base sequence represented by "TTAGGG". Thus, the tag sequence may be partially complementary to the base sequence represented by "TTAGGG" so long as it does not hybridize thereto, or may also be unrelated to the base sequence represented by "TTAGGG". The length of such a tag sequence may be 1 to 40 bases, preferably 5 to 30 bases in view of high amplification efficiency. The conditions under which hybridization does not occur may be, for example, 30 to 120° C., preferably 37 to 90° C.

(2) Detection of Telomerase Activity

To detect the oligonucleotide (DNA or RNA) thus obtained in a large amount, the present invention utilizes the hybridization protection assay (HPA) method developed by Gen-Probe Inc.: Japanese Patent Application Laying Open No. 2-503147.

The HPA method involves the use of an oligomer labelled with a non-radioactive labelling substance as a probe and the detection of chemiluminescence from said non-radioactive labeling substance when said probe hybridizes to the DNA or RNA to be detected. The characteristic of this method is to selectively hydrolyze the labelling substance of free probes to deactivate the labelling substance, rather than the physical separating operation such as washing carried out to distinguish hybridized probes from non-hybridized free probes. Accordingly, a desired target (nucleic acid or oligonucleotide) can be detected by simple operations within a short period of time.

The non-radioactive labelling substance may include, for example, acridinium esters, hereinafter referred to as "AE", luminol, isoluminol, pyrogallol, protohaemin, aminobutylethyl-n-isoluminol, aminohexylethyl-n-ethyl-isoluminol, and acridine derivatives.

The acridine derivatives may include, for example, those represented by the following formula I:

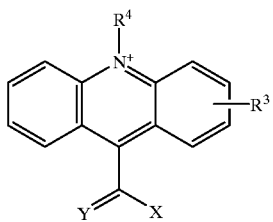

(I)

wherein X denotes a halogen, or a group represented by the following formula II:

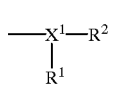

(II)

in which $X^1$ is a nitrogen, phosphorus, boron or arsenic atom, $R^1$ is an alkoxy or aryloxy group, or a substituted or unsubstituted alkyl, alkenyl or aryl group, and $R^2$ is a hydrogen atom, or, an alkoxy or aryloxy group, or a substituted or unsubstituted alkyl, alkenyl or aryl group, or the following formula III:

 (III)

in which $X^2$ is an oxygen or sulfur atom and $R^2$ is as defined above, Y denotes an oxygen or sulfur atom, or NH, $R^3$ denotes a hydrogen atom, an amino, hydroxy, thiol, carboxylic acid, halogen, nitro, alkoxy or aryloxy group, or a substituted or unsubstituted acetyl, alkyl, alkenyl or aryl group, $R^4$ denotes a substituted or unsubstituted alkyl, alkenyl or aryl group, and at least one of $R^1$, $R^2$, $R^3$ and $R^4$ comprises a reactive site capable of chemical bonding. However, the present invention is not limited to the above described non-radioactive labelling substances.

The halogen includes, for example, fluorine, chlorine, bromine, iodine and astatine. The alkyl includes those having 1 to 20 carbon atoms, preferably 1 to 5 carbon atoms, such as methyl, ethyl, propyl, butyl and amyl. The alkenyl includes those having 1 to 10 carbon atoms, preferably 1 to 5 carbon atoms, such as vinyl and allyl. The aryl includes, for example, phenyl, tolyl, naphthyl and xylyl. The alkoxy includes those having 1 to 10 carbon atoms, preferably 1 to 5 carbon atoms, such as methoxy and ethoxy. The aryloxy includes, for example, phenoxy and naphthoxy.

The probe used in the present invention is not particularly limited so long as it is extended through the telomerase extension reaction and is complementary to DNA or RNA amplified therefrom. Generally, the probe used comprises 10 to 40 bases, preferably 15 to 30 bases. The oligonucleotide used in the probe may be synthesized by the conventional phosphoamidite method using a commercially available DNA synthesizer. An amino linker for labelling DNA with AE or other labelling substance has been introduced during the chemical synthesis.

The DNA probe is labelled with AE or other labelling substance, for example, by reaction of the amino linker introduced during the DNA synthesis with an N-hydroxysuccinimide ester of AE.

The labelling site of AE or other labelling substance may vary freely depending upon the position of the amino linker introduced during the DNA synthesis: Yukio Matsuoka, et al., Clinical Pathology, Special Edition, Vol. 85, pp. 82–91 (1990).

i) Detection Using AE

As shown in FIG. 2, when the AE-labelled probe hybridizes to the amplified DNA or RNA (target), the AE is stabilized between the double helix of DNA. Even if hydrolysis is carried out for a given period of time, the ester linkage of AE is protected. Therefore, upon addition of an alkali and hydrogen peroxide, the acridinium ester is capable of generating chemiluminescence, from which the target can be detected: FIG. 2 (1).

On the other hand, the AE can not be stabilized between the double helix when the probe does not hybridize to the target. Under this condition, the ester linkage of AE undergoes hydrolysis. As a result, no chemiluminescence is generated and the target can not be detected: FIG. 2 (2).

The probe used in the detection may include, for example, probe 1 (SEQ ID NO: 3), probe 2 (SEQ ID NO: 4), probe 3 (SEQ ID NO: 5), probe 4 (SEQ ID NO: 6), probe 5 (SEQ ID NO: 7), probe 6 (SEQ ID NO: 8), probe 7 (SEQ ID NO: 9), and probe 8 (SEQ ID NO: 10). These probes 1 and 2, probes 3 and 4, probes 5 and 6, and probes 7 and 8 have the same sequence, respectively, but different binding sites of AE. The binding sites of AE were between 14th and 15th bases for probe 1, between 15th and 16th bases for probe 2, between 9th and 10th bases for probe 3, between 10th and 11th bases for probe 4, between 13th and 14th bases for probe 5, between 14th and 15th bases for probe 6, between 15th and 16th bases for probe 7, and between 16th and 17th bases for probe 8, respectively, in the respective base sequences.

The probe labelled with AE is added to the DNA or RNA amplified in the above manner (1) and incubated at 60° C. for 5 to 30 minutes. To avoid chemiluminescence from unreacted probes, a hydrolysing reagent is added and incubated at 60° C. for 5 to 10 minutes. After incubation, the chemiluminescence of AE is detected using a photomultiplier such as Reader I.

HPA using AE may also be carried out by using a kit from Gen-Probe Inc. according to the specification.

ii) Detection Using an Acridine Derivative or Other Non-radioactive Labelling Substance To a solution containing the DNA or RNA, an appropriate amount of the probe labelled with the acridine derivative is added to react. After the reaction and subsequent hydrolysis, the chemiluminescence is detected as in the case of AE.

For luminol, isoluminol, pyrogallol, protohaemin, aminobutylethyl-n-isoluminol, and aminohexylethyl-n-ethyl-isoluminol, the above procedures or other methods may also be applied to detect chemiluminescence.

In detecting the telomerase activity according to the present invention, after an oligonucleotide sequence extended through the DNA extension reaction by a telomerase is amplified, the resulting amplified product can also be detected without using any radioactive labelling substance. For instance, a fluorescent substance such as FITC (Fluorescein Isothiocyanate), Rhodamine or Coumarin may be used to provide a fluorescent label at the 5' end of the primer 1 (SEQ ID NO: 1). After electrophoresis, the amplified product can be detected by a given detector.

According to the method of the present invention, detection results can be obtained with a higher sensitivity as compared with conventional detection methods.

Further, since no radioactive substance is used, no special disposal equipment is required. Separation of the reaction products from non-incorporated radioactive substances as in the prior arts is not necessary. Consequently, the detection can be carried out rapidly. Thus, results can be obtained within one hour from the start of HPA operation; therefore, all detection processes may be completed within one day.

According to the present invention, telomerase activity can be easily detected with a good reproducibility and a large amount of sample may be dealt with.

The detection of telomerase activity in clinically obtained tissues or the like using the method of the present invention is usuful in the detection of cancer cells and diagnosis of cancer and is very useful in monitoring the progress of cancer or prognosis of treatment.

The cancer cells to be detected herein may include, for example, those contained in specimens obtained invasively or non-invasively.

The term "invasively" used herein means that the collection of specimens is associated with bleeding when the specimens are taken by physically or chemically damaging or wounding human tissues or organs. For instance, examples of invasive methods include, for example, operation, excision of tissues by an endoscope, biopsy by a needle, and injection for exsanguinating. Specimens obtained invasively may include urinary bladder tissues, prostate gland tissues, uterus tissues, uterocervix tissues, udder tissues, pancreas tissues, liver tissues, large intestine tissues, stomach tissues, lung tissues, peripheral blood cells, kidney tissues, skin tissues, esophagus tissues, brain tissues and oral cavity tissues.

On the other hand, according to the present invention, specimens can be taken without physically or chemically damaging or wounding human tissues or organs; then, no bleeding is referred to as "non-invasive". For example, non-invasive methods may be exemplified by collection of excretions from bodies, and washing of organs. Specimens obtained non-invasively may include, for example, urine, prostate gland juice, urinary bladder wash, uterus smear, pancreatic juice, duodenum juice, feces, oral cavity wash, enteron wash, saliva and sputum.

(3) Kit for the Detection of Cancer Cells and/or the Diagnosis of Cancer

The kit of the present invention comprises a reagent used in the method for the detection of telomerase according to the present invention, that is, an oligonucleotide primer comprising at least a base sequence represented by "AGNGTT" wherein N is A, T, G or C at the 3' end, an oligonucleotide primer comprising the base sequence represented by SEQ ID NO: 21 or an oligonucleotide primer comprising a base sequence having at least one nucleotide deleted, substituted or added in the base sequence of the primer, and a probe labelled with a non-radioactive labelling substance.

The kit of the present invention further comprises a primer having a promoter added to the 5' end of said oligonucleotide primer.

These kits are used to detect the telomerase activity, to detect cancer cells, or to diagnose cancer.

BEST MODE FOR CARRYING OUT THE INVENTION

Figure 1:
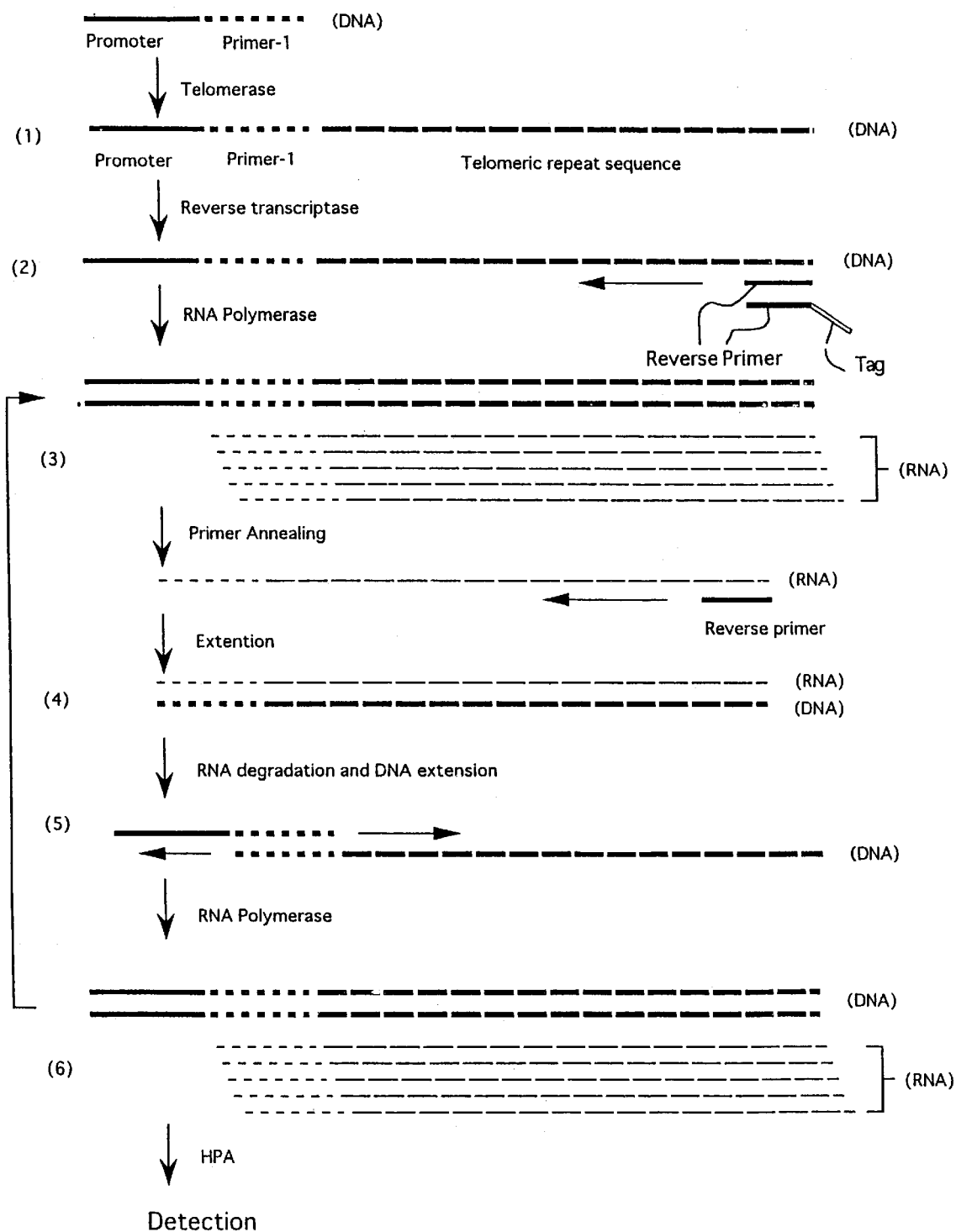
FIG. 1 schematically illustrates the procedures for detecting the telomerase activity using RNA synthesis reaction with RNA polymerase.
Figure 2:
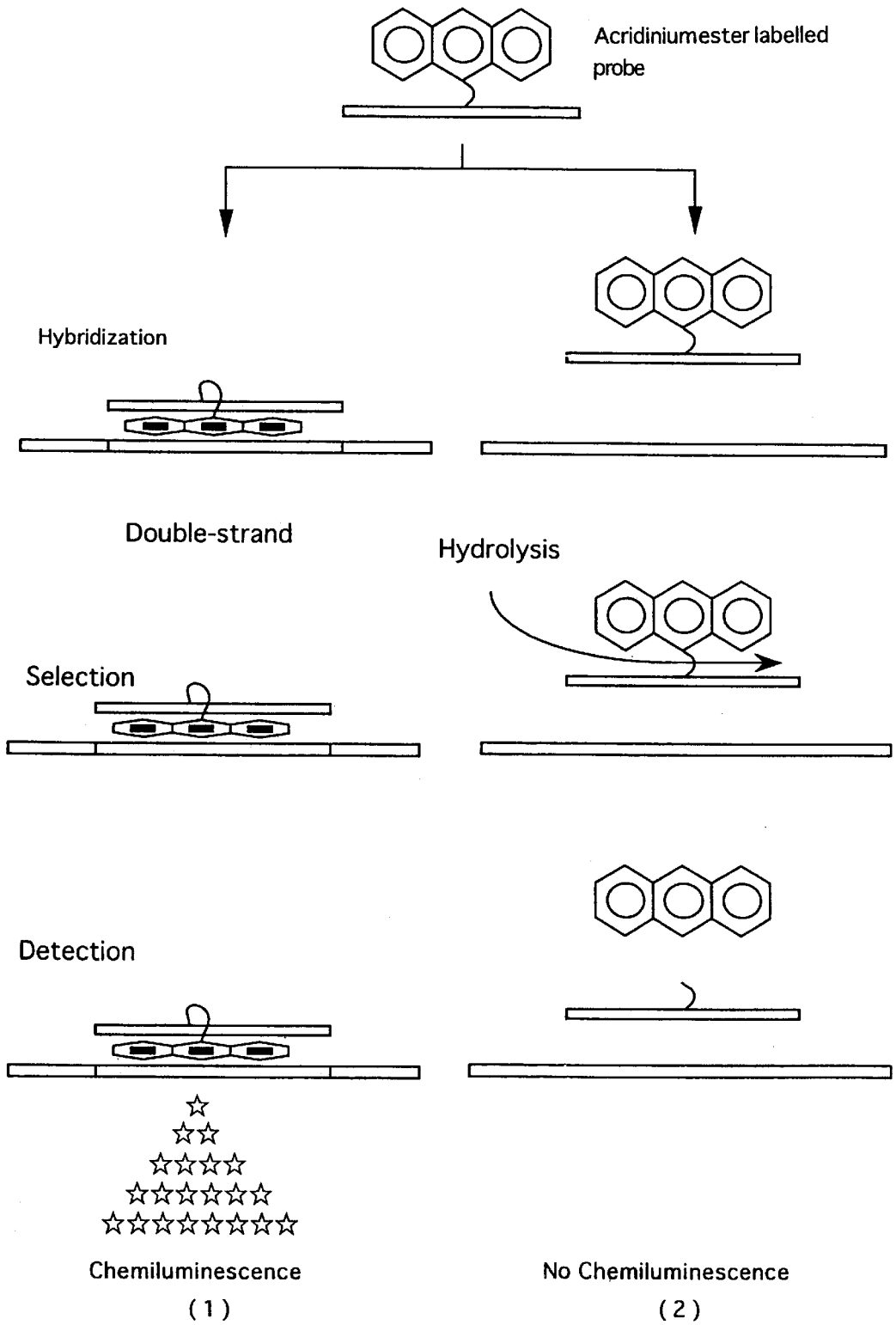
FIG. 2 shows the principle of HPA method.

Hereinafter, the present invention will be illustrated by way of examples. However, the present invention is not limited to these examples.

EXAMPLE 1

Amplification by TRAP Method and Detection of Telomerase Activity by HPA Method

I. Materials and Method (1) Preparation of Extracts Containing Telomerases from Cell Lines Cancer cell lines K562 and MKN1 were cultured. The culture was centrifuged and the supernatant was removed. Then, 200 µl of an ice-cooled lysis buffer (10 mM Tris, 1 mM $MgCl_2$, 1 mM EGTA, 0.5% CHAPS (Cholamidopropyl-dimethyl-ammonio-1-propanesulfonate), 10% Glycerol, 5 mM β-mercaptoethanol, 0.1 mM AEBSF (4-(2-aminoethyl)-benzenesulfonyl fluoride hydrochlorine: pH 7.5) was added and stirred 4 to 5 times with a pipette. The mixture was allowed to stand on ice for 30 minutes and centrifuged at 15,000 rpm, 4° C. for 20 minutes and the supernatant was transferred to another tube (corresponding to 500 cells per µl).

(2) Synthesis of Primer

Primers represented by SEQ ID NOs: 1 and 2 were synthesized as primers 1 and 2 (reverse primer), respectively, using a DNA synthesizer (ABI).

(3) TRAP Method

Telomerase was extracted from the cancer cells and TRAP method was carried out as follows.

First, the following reagents were added to a tube:
5 µl 10× TRAP-PCR buffer (0.2 M Tris, 15 mM $MgCl_2$, 680 mM KCl, 0.05% Tween 20, 5 mM EGTA pH 8.3);
0.25 µl 10 mM dNTPs;
2 µl primer 1 (50 ng/µl) (SEQ ID NO: 1);
0.2 µl T4g32 protein (5 µg/µl) (Boehringer Mannheim); and
0.4 µl Ampli Taq (5 U/µl).

When $^{32}P$ is used, 0.4 µL of α-dCTP (3,000 Ci/mmol; 4 µCi/assay) was added.

The total volume was adjusted to 48 μl with H₂O treated with DEPC (diethyl pyrocarbonate). Two (2) μl of the extract containing telomerase was added, stirred and incubated at 20° C. for 30 minutes. One drop of mineral oil was layered and incubated at 90° C. for 3 minutes. Two (2) μl of the reverse primer (SEQ ID NO: 2) (50 ng/μl) was added and PCR was carried out. In the PCR, 31 cycles of 94° C. for 40 seconds, 50° C. for 40 seconds and 72° C. for 60 seconds were repeated and finally incubation was effected at 72° C. for 120 seconds (IWAKI TSR-300).

Samples used were 10-, 100- and 1,000-fold dilutions of two extracts prepared in (1) with the lysis buffer (corresponding to 1,000, 100, 10 and 1 cell per tube).

(4) Detection by HPA i) Comparison Test of Probe Sensitivity

To compare the sensitivity of each probe in the present invention, HPA was carried out in a pure system using a synthetic oligomer as a target.

The target oligomer (SEQ ID NO: 12) was stepwise diluted with H₂O to 500, 50, 10, 5, 1 and 0.5 fmol/10 μl. Ten (10) μl of the target at each concentration was added to a tube and 90 μl of H₂O was added. After 100 μl of a probe liquid adjusted with a hybridization liquid to a chemiluminescence amount of 3.0×10⁶ rlu (relative light units)/100 μl was added, the mixture was incubated at 60° C. for 20 minutes. To this 300 μl of DH liquid (600 mM boric acid, 182 mM sodium hydroxide, 1% Triton X-100) was added, stirred and incubated at 60° C. for 10 minutes. After incubation, the tube was quenched in water for about 3 minutes and the chemiluminescent amount was measured by Reader I (Gen-Probe).

Figure 3:
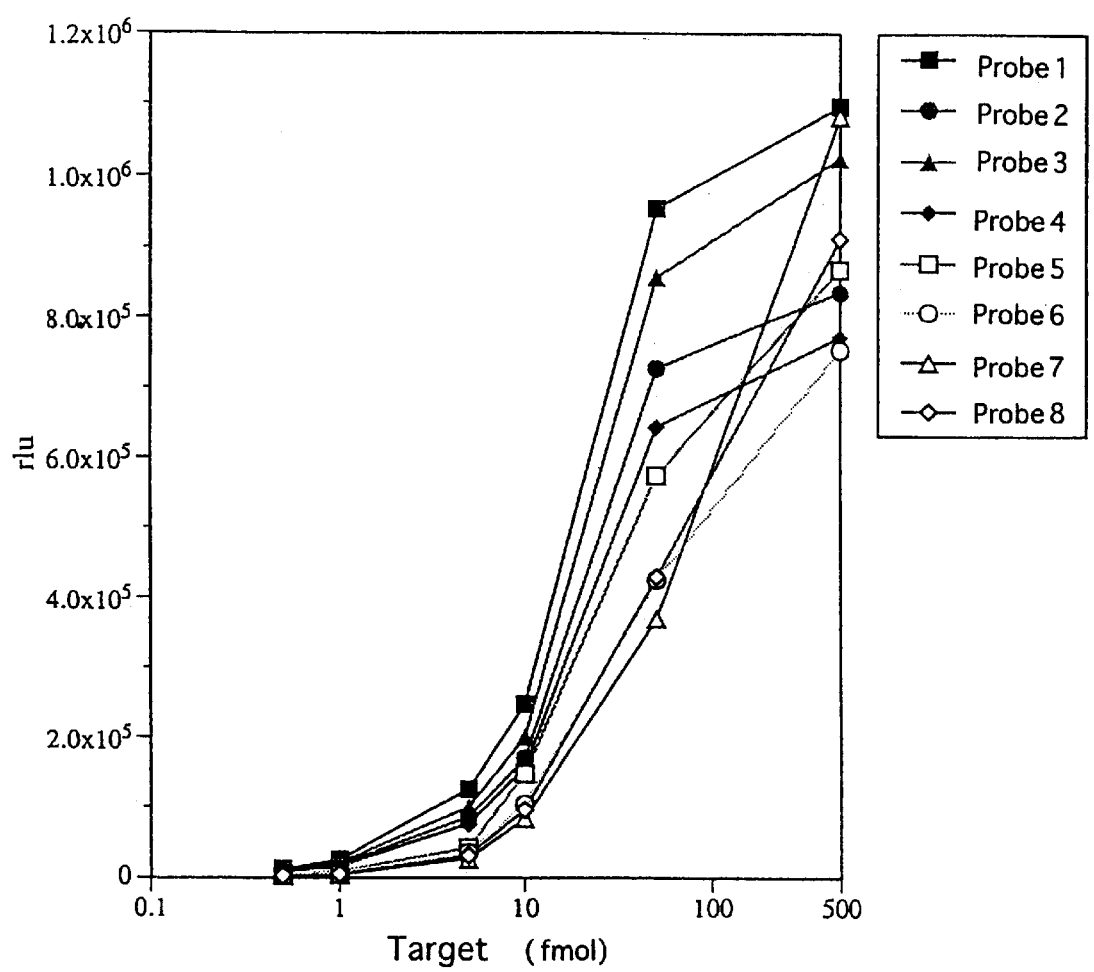
FIG. 3 shows the results of measurement of sensitivities of probes 1 to 8.
Figure 4:
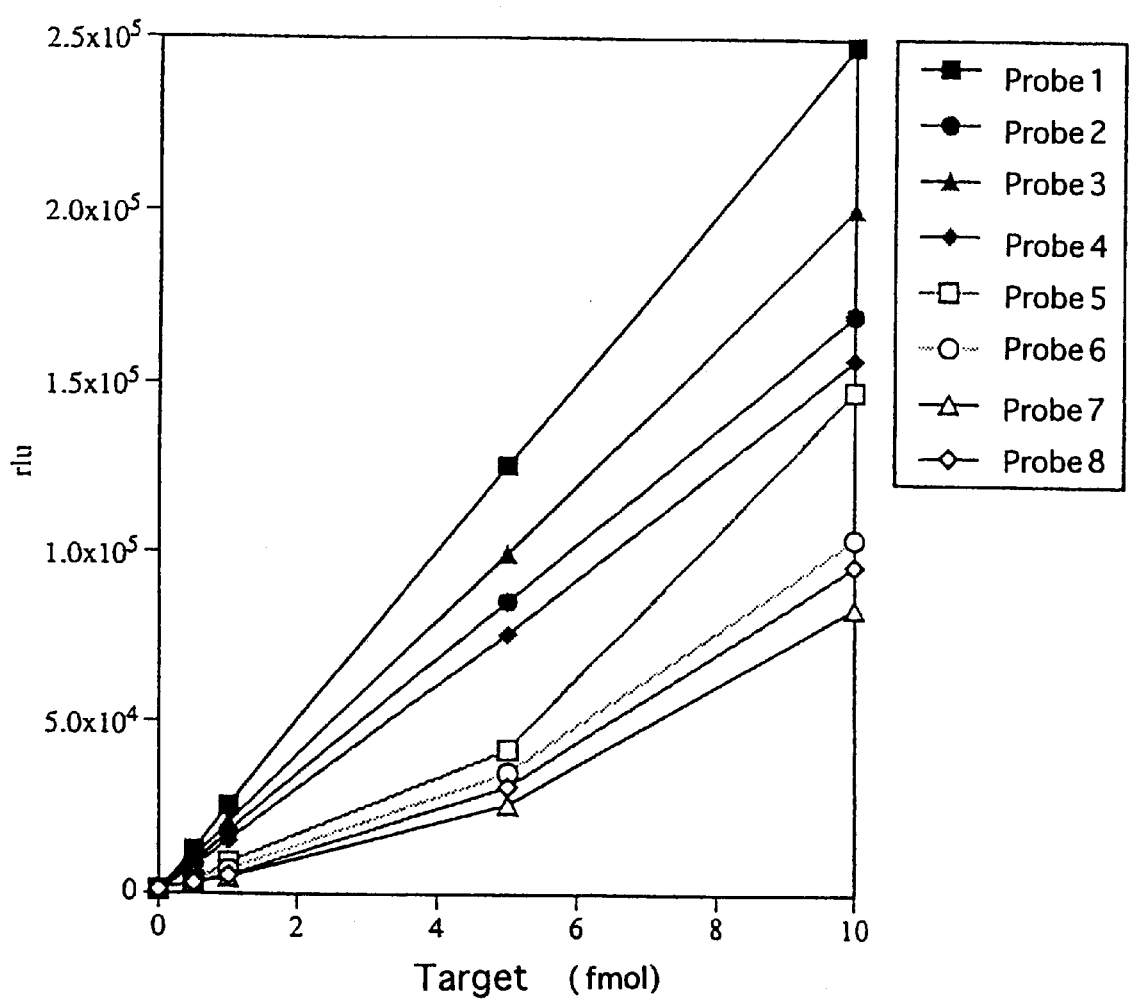
FIG. 4 shows the results of measurement of sensitivities of probes 1 to 8.

As shown in FIGS. 3 and 4, the detection sensitivity of HPA in the pure system was 0.5 to 1 fmol in the case of a cut-off value 10,000 rlu, and the best and second best sensitive probes were probes 1 and 3, respectively. Accordingly, probe 1 was chosen in the present invention as a preferred probe for the detection of telomerase activity from among the probes 1 to 8 which may be used as a probe. FIG. 4 is an enlarged graph of that of FIG. 3 in the range of 0 to 10 fmol target.

ii) Detection of Telomerase Activity

The TRAP product (5 μl) was added to a tube containing 100 μl H₂O and denatured at 95° C. for 5 minutes. After quenching in ice water for about 3 minutes, 100 μl of probe 1 (SEQ ID NO: 3, 3×10⁶ rlu/100 μl) was added. The mixture was incubated at 60° C. for 20 minutes and then 300 μl of DH liquid was added, stirred and incubated at 60° C. for 10 minutes. Subsequently, the tube was quenched in water for about 3 minutes and returned to room temperature. The amount of chemiluminescence was measured by Reader I.

As a control, detection was also effected by a conventional method (electrophoresis followed by labelling with ³²P and SYBR Green staining (FMC) as non-radioactive labelling). Thus, the TRAP products (corresponding to 1,000 and 100 cells) were diluted 10-, 100- and 1,000-fold, electrophoresed and stained with ³²P or SYBR Green and the detection sensitivity was measured and compared with the results by the HPA method.

The electrophoresis was effected on 12% polyacrylamide gel using 10 μl of the TRAP product (at 100 V for 15 minutes, at 300 V for about one hour). In the case of ³²P, the electrophoresed gel was dried at 80° C. for 30 minutes. Then, autoradiography was done at −80° C. and the presence or absence of ladders was checked. In the SYBR Green staining, SYBR Green was diluted 10,000 fold with 0.5× TBE (0.045 M Tris-borate, 0.001 M EDTA (pH 8.0)) and used to stain for about 30 minutes, and then ladders were observed under UV.

II. Results

Figure 5:
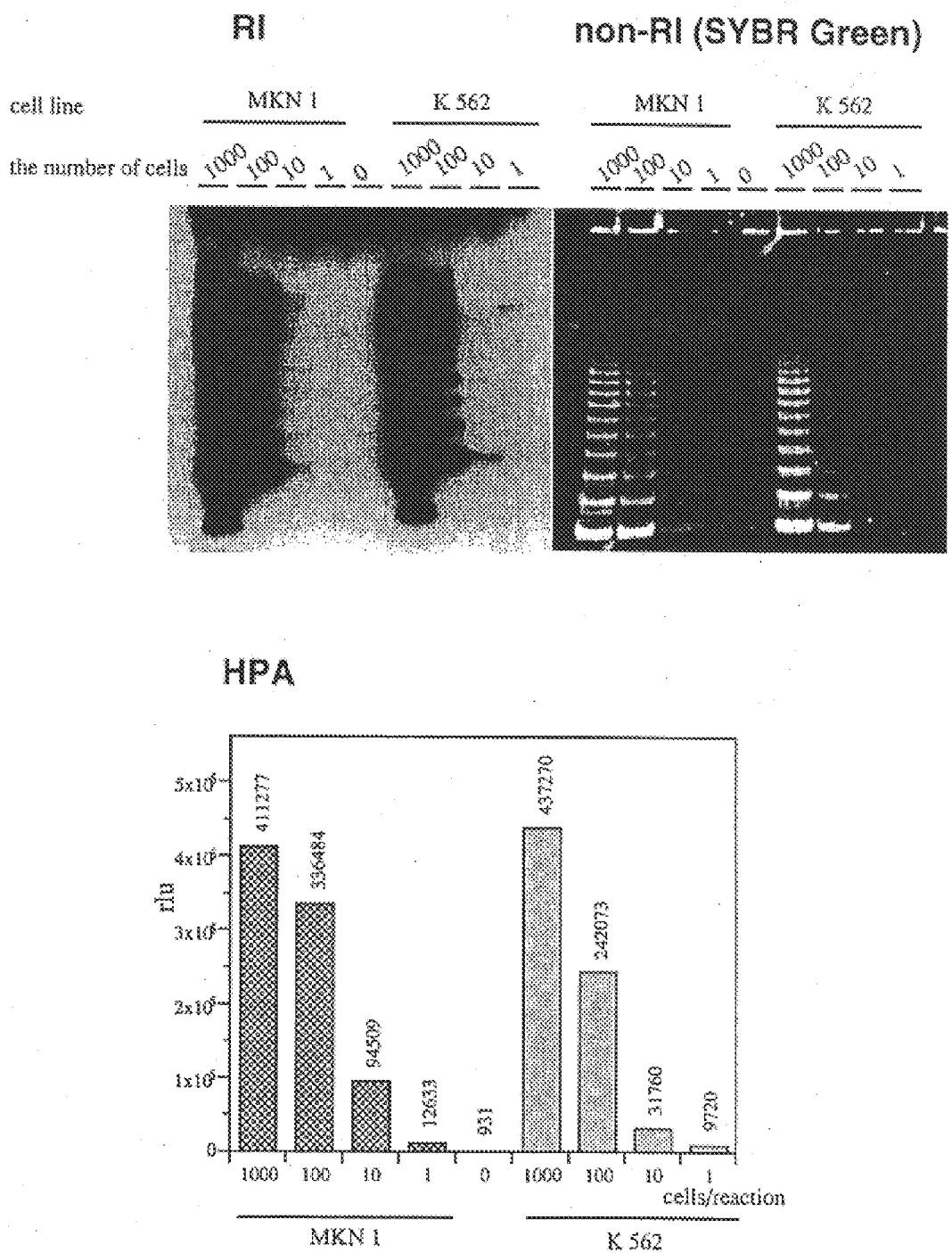
FIG. 5 shows comparative test results of sensitivities in detection by the HPA and conventional methods, where (1) is a result of electrophoretic photograph with $^{32}P$; (2) is a result of electrophoretic photograph by SYBR Green staining; and (3) is a result of HPA.

Referring to FIG. 5, when diluted extract samples containing telomerase corresponding to 1,000, 100, 10 and 1 cell were subjected to TRAP, ladders could be detected up to 10 cells with ³²P labelling (FIG. 5 (1)) and up to 10 cells (MKN1) and 100 cells (K562) with SYBR Green staining (FIG. 5 (2)). For HPA detection sensitivity with a cut-off value of 10,000 rul, on the other hand, up to 1 cell (MKN1) and 10 cells (K562) were positive (FIG. 5 (3)).

Figure 6:
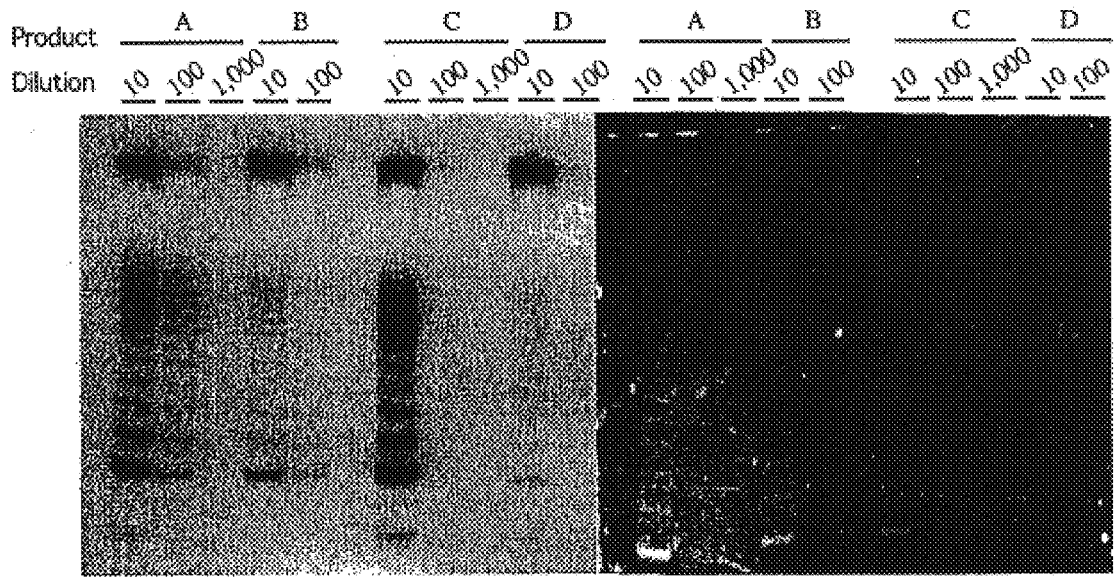
FIG. 6 shows comparative test results of sensitivities using TRAP products in detection by the HPA and conventional methods, where (1) is a result of electrophoretic photograph with $^{32}P$; (2) is a result of electrophoretic photograph by SYBR Green staining; and (3) is a result of HPA.
Figure 6:
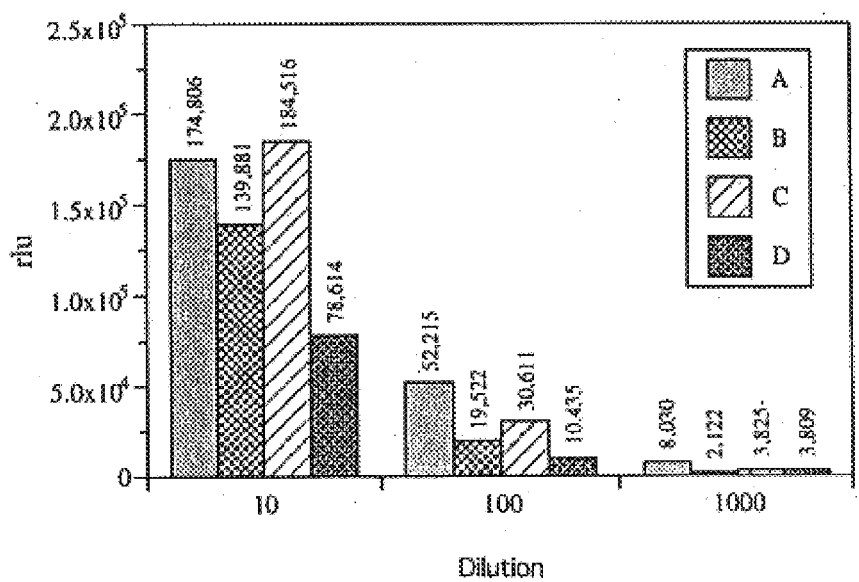

Referring to FIG. 6, sensitivities of detection were compared using TRAP products from the extracts corresponding to 1,000 and 100 cells after 10-fold dilution. In the case of ³²P labelling, ladders could be detected up to 100-fold dilution of TRAP product corresponding to 1,000 cells (FIG. 6 (1) A), while ladders were observed only up to 10 fold dilution of TRAP product coresponding to 100 cells (FIG. 6 (1)B). In the case of SYBR Green staining, ladders could be detected only up to 10 fold dilution of both TRAP products corresponding to 1,000 and 100 cells (FIG. 6 (2)). In HPA, both 1,000 and 100 cells-corresponding TRAP products were positive up to 100 fold dilution (FIG. 6 (3)).

From these results, it was confirmed that the detection sensitivity of HPA is substantially same as 32p and at least 10 fold higher than that of SYBR Green staining.

EXAMPLE 2

Amplification by RNA Synthesis and Detection of Telomerase Activity by HPA (1)

The present inventors used a primer (referred to "T7 primer", SEQ ID NO: 11 in this example) comprising T7 RNA polymerase promoter (SEQ ID NO: 13) linked to the 5' end of primer 1 to carry out extension reaction by telomerase activity to synthesize a single stranded DNA containing T7 RNA promoter region. This single stranded DNA was used as a target to effect TMA and eventually RNA was synthesized in a large amount.

I. Materials and Method (1) Amplifying Reagent 4 mM ATP, disodium trihydrate
4 mM CTP, disodium dihydrate
4 mM GTP, disodium monohydrate
4 mM UTP, disodium dihydrate
40 mM Trizma, base
12.5 mM Potassium chloride
1 mM DATP, disodium
1 mM dCTP, trisodium
1 mM dGTP, trisodium
1 mM dTTP, trisodium, pH 7.5±0.1
18 mM Magnesium chloride (2) Enzyme Reagent 1 mM EDTA
140 Mm Trizma, base
70 mM Potassium chloride
10% Triton X-102
2% Glycerol
2.000 U RTase
2,000 U T7 RNA polymerase (3) Primer Primer of SEQ ID NO: 11 (10 pmol/assay)
Primer of SEQ ID NO: 21 (30 pmol/assay)

To a tube, 50 μl of the amplifying reagent containing primer of SEQ ID NO: 11 was added and 2 μl of a diluted K562 cell extract containing telomerase was added. The mixture was incubated at 20° C. for 30 minutes. To this, 200

μl of mineral oil and 25 μl of 2 fold concentrated amplifying reagent containing primer of SEQ ID NO: 21 were added and incubated at 95° C. for 5 minutes, at 60° C. for 10 minutes and then at 45° C. for 5 minutes. Then, 25 μof the enzyme reagent was added and incubated at 45° C. for 2 hours. After amplification, 10 μl of TMA product was added to a tube containing 100 μl of H$_2$O and 100 μl of probe (3×10$^6$ rlu/100 μl) was further added.

The probe used had the following sequence and was labelled with AE between the 14th base (T) and 15th base (A):

Sequence:
5'-CTAACCCTAACCCTAACCCTAACCCTAACTCT-3' (SEQ ID NO: 29)

After incubation at 65° C. for 20 minutes, 300 μl of DH liquid was added and stirred. The tube was incubated at 65° C. for 10 minutes and then quenched in water for about 3 minutes. After returning to room temperature, the amount of chemiluminescence was measured by Reader I.

II. Results

Figure 9:
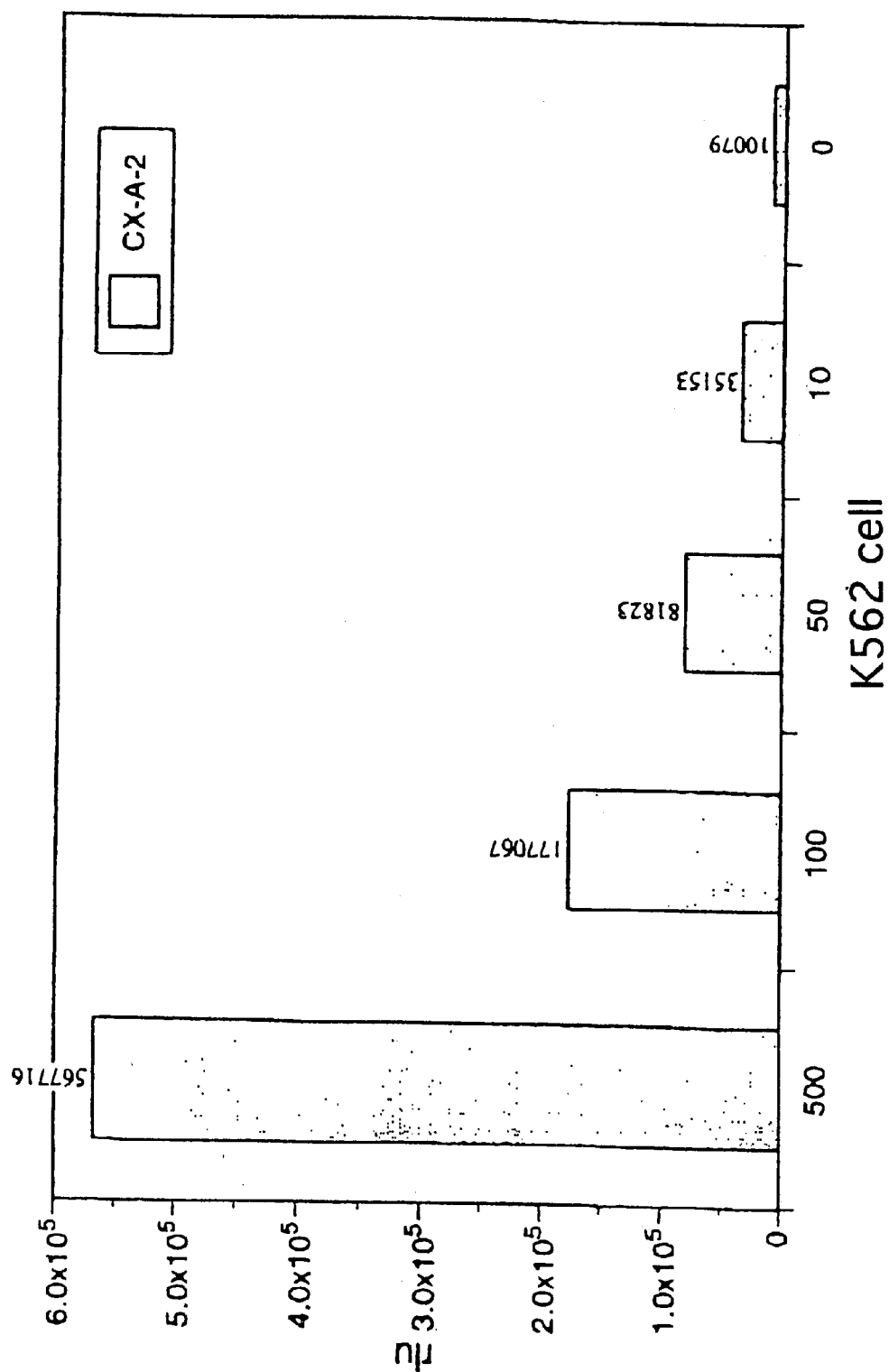
FIG. 9 shows detection results of telomerase activity using an oligonucleotide primer having a tag sequence added.

As shown in FIG. 9, even K562 cell extracts corresponding to 10 cells were positive. Thus, telomerase activity could be detected with a high sensitivity.

EXAMPLE 3

Amplification by RNA Synthesis and Detection of Telomerase Activity by HPA (2)

In this example, the telomerase activity was detected in a similar manner to Example 2 using a tag sequence reverse primer in the RNA synthesis.

However, the amplifying temperature and period of time ater addition of the enzyme reagent were 40° C. and 75 minutes.

The following primers were used. Small characters represent tag sequences.
CX primer: CCCTTACCCTTACCCTTACCCTAA (SEQ ID NO: 2)
CX-A-2: TTACCCTTACCCTTACCCT (SEQ ID NO: 21)
CX-A-2-III: acgtagcgttagTTACCCTTACCCTTACCCT (SEQ ID NO: 22)
CX-A-2-II-11: cgtagcgttagTTACCCTTACCCTTACCCT (SEQ ID NO: 23)
CX-A-2-II-10: gtagcgttagTTACCCTTACCCTTACCCT (SEQ ID NO: 24)
CX-A-2-II: tagcgttagTTACCCTTACCCTTACCCT (SEQ ID NO: 25)
CX-A-2-II-8: agcgttagTTACCCTTACCCTTACCCT (SEQ ID NO: 26)
CX-A-2-II-7: gcgttagTTACCCTTACCCTTACCCT (SEQ ID NO: 27)
CX-A-2-1: cgttagTTACCCTTACCCTTACCCT (SEQ ID NO: 28)

The K562 cells were used as the object to be detected and adjusted to a given number of cells prior to the test.

Figure 7:
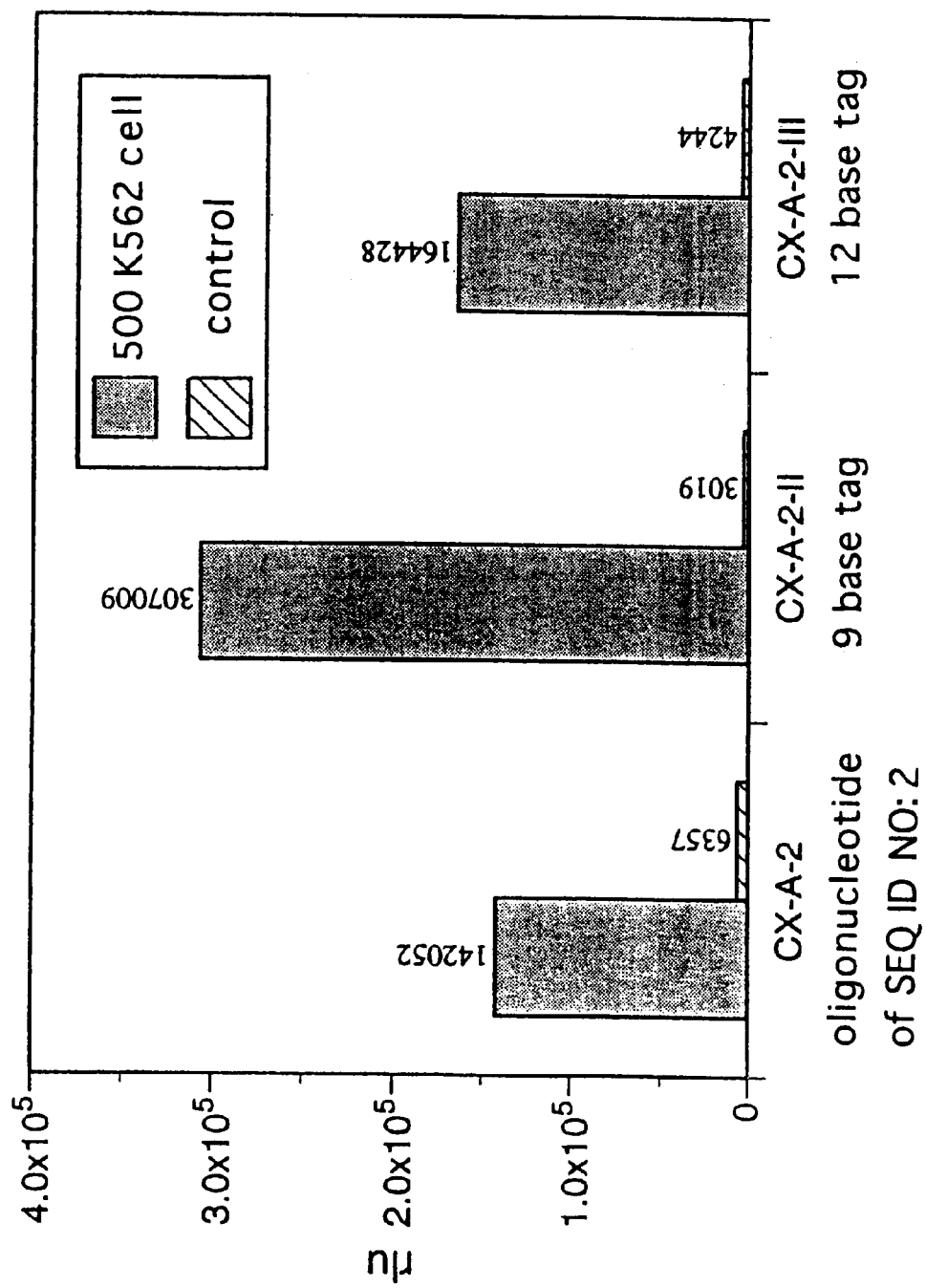
FIG. 7 shows detection results of telomerase activity using an oligonucleotide primer having a tag sequence added.

As shown in FIG. 7, when 500 K562 cells were subjected to the detection test, primer CX-A-2-II to which a tag of 9 bases was added (SEQ ID NO: 25) and primer CX-A-2-III to which a tag of 12 bases was added (SEQ ID NO: 22) increased the RNA synthesis efficiency and enhanced the detection sensitivity.

Figure 8:
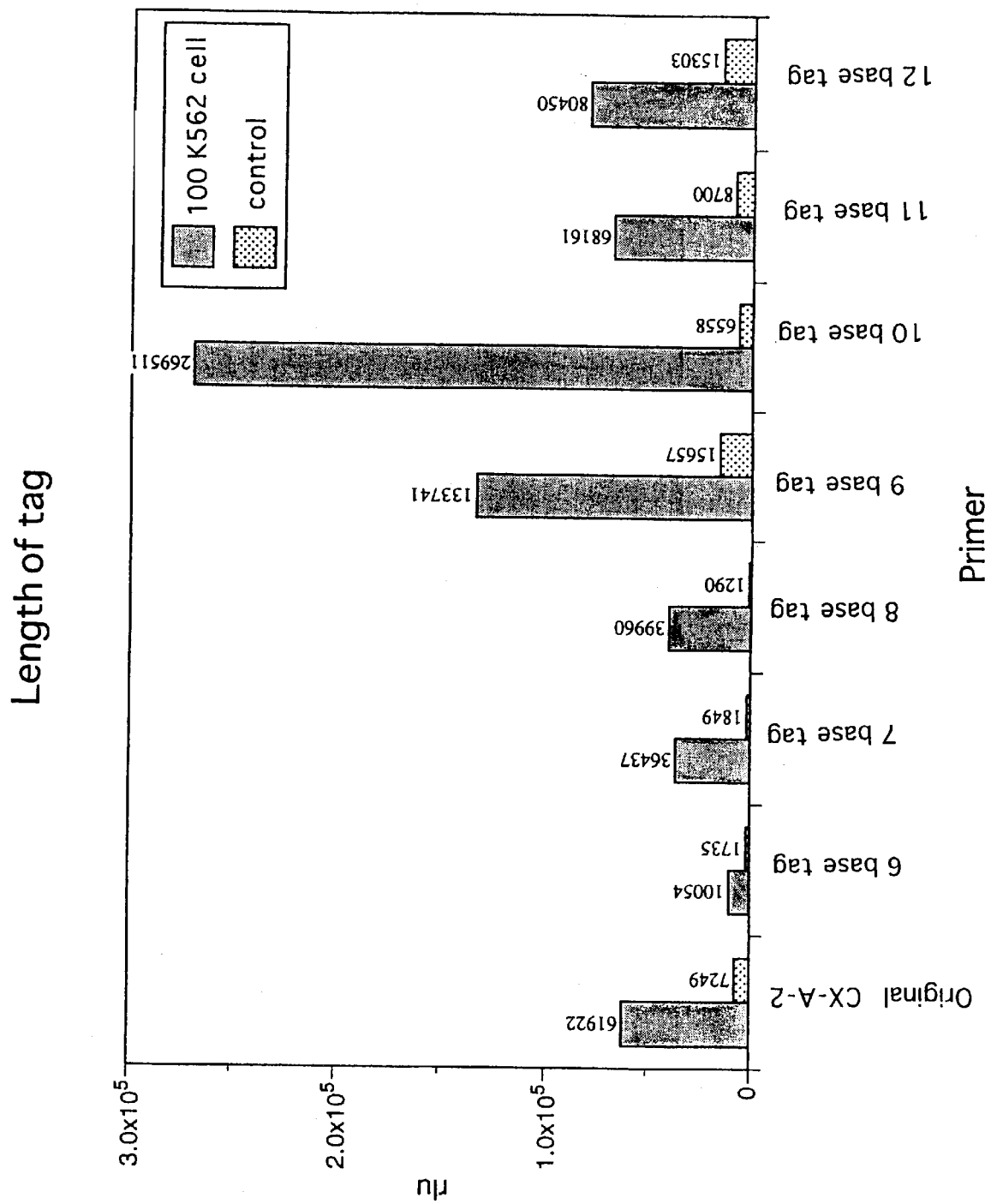
FIG. 8 shows detection results of telomerase activity using an oligonucleotide primer having a tag sequence added.

When the number of K562 cells was reduced to 100 cells, the RNA synthesis efficiency was increased with primers to which a tag of 9 to 12 bases was added (SEQ ID NOs: 22 to 25), indicating that even smaller cells could enhance the detection sensitivity (FIG. 8).

Figure 10:
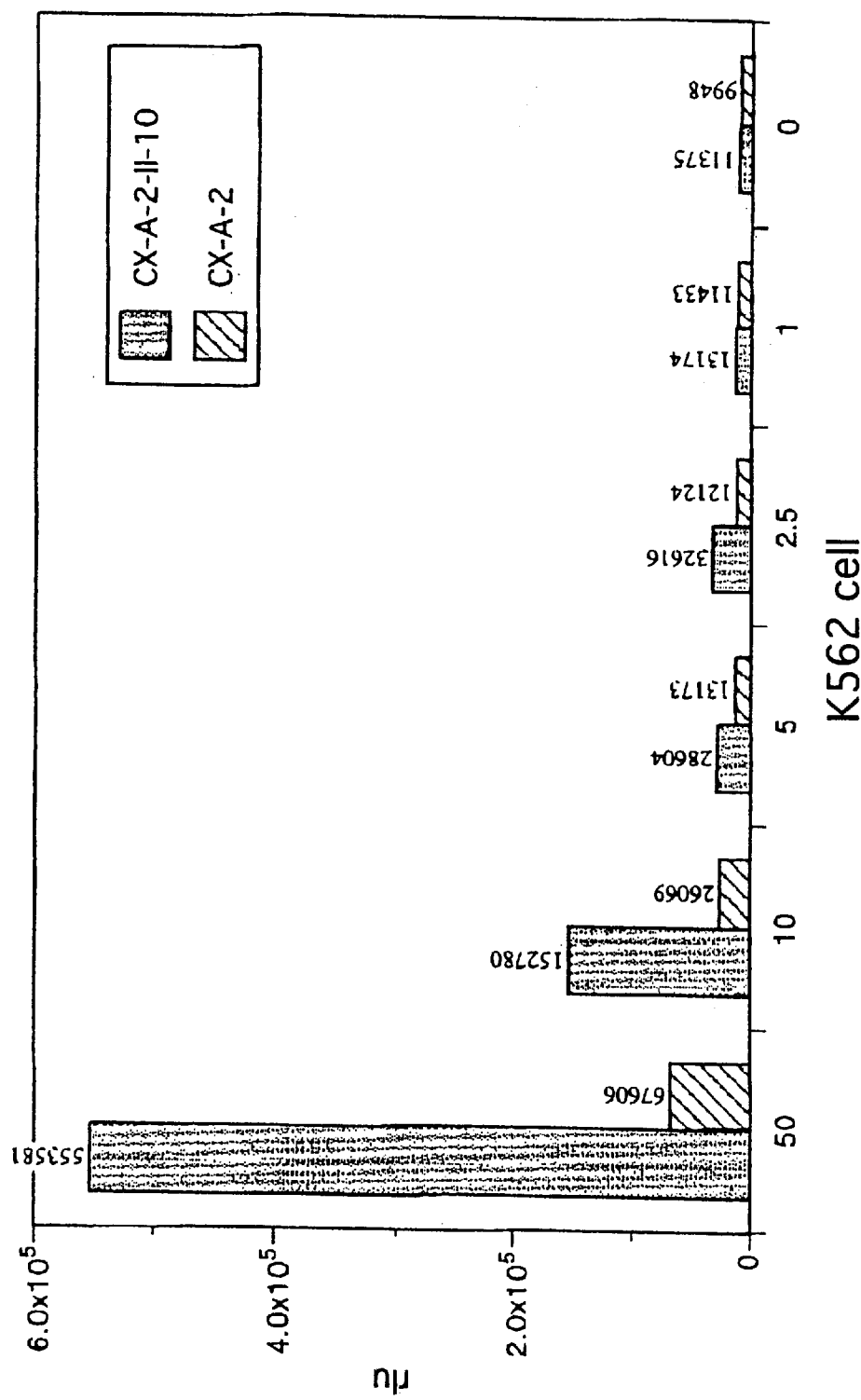
FIG. 10 shows detection results of telomerase activity using an oligonucleotide primer having a tag sequence added.

Further, when 0 to 50 K562 cells were prepared and the RNA synthesis reaction and detection were carried out using primer CX-A-2-II-10 (SEQ ID NO: 24) to which a 10 base tag was added, even 2.5 cells were detected as shown in FIG. 10, indicating that the method of the present invention could detect cells with a high sensitivity.

EXAMPLE 4

Detection of Cancer Cells

I. Cells and Tissues (1) Cancer Cell Lines

HeLa cells (uterocervix cancer), U937 (histiocytic lymphoma), K562 (chronic myelogenous leukemia), U373MG (glioblastoma), T98G (glioblastoma), A172 (glioblastoma), MCF-7 (breast cancer), HT-1080 (fibrosarcoma), LoVo (large intestine cancer), WiDr (large intestine cancer), SW857 (large intestine cancer), and VA-4 (SV-40 transformed fibroblast) were cultured in 10% FCS containing RPMI medium. Normal cells were taken from normal, healthy peripheral nucleus (MNC) and fibroblast (HNF).

(2) Liver Cancer Tissues

Surgically excised tissues obtained from 83 cases of liver cancer and liver diseases were frozen in liquid nitrogen and stored at −80° C. till use.

(3) Large Intestine Cancer Tissues

Surgically excised tissues obtained from 26 cases of large intestine cancer were frozen in liquid nitrogen and stored at −80° C. till use.

II. TRAP Method

According to the conventional methods, extracts containing telomerase activity were obtained from said cells or tissues in a similar manner to Example 1.

For the cell extracts of each of cancer cell lines and large intestine cancer tissues and liver cancer tissues, the extension reaction by telomerase and amplification of gene were done.

The extension reaction by telomerase was done at 20° C. for 30 minutes using the oligonucleotide represented by SEQ ID NO: 1. In the amplification of gene, the oligonucleotide represented by SEQ ID NO: 2 was used, 31 cycles of reactions at 94° C. for 40 seconds, at 50° C. for 40 seconds and at 72° C. for 60 seconds were repeated, and finally incubation was done at 72° C. for 120 seconds (IWAKI TSR-300).

III. HPA

The amplified product obtained by TPAP method was denatured at 94° C. for 5 minutes and an AE labelled probe which hybridized to the amplified product was added and reacted at 60° C. for 20 minutes. Then, DH buffer was added and reacted at 60° C. for 10 minutes.

For the reaction mixture, the amount of chemiluminescence (RLU, relative light units) was measured by a luminometer at a rate of 2 seconds per tube.

IV. Quantitative HPA

Figure 11:
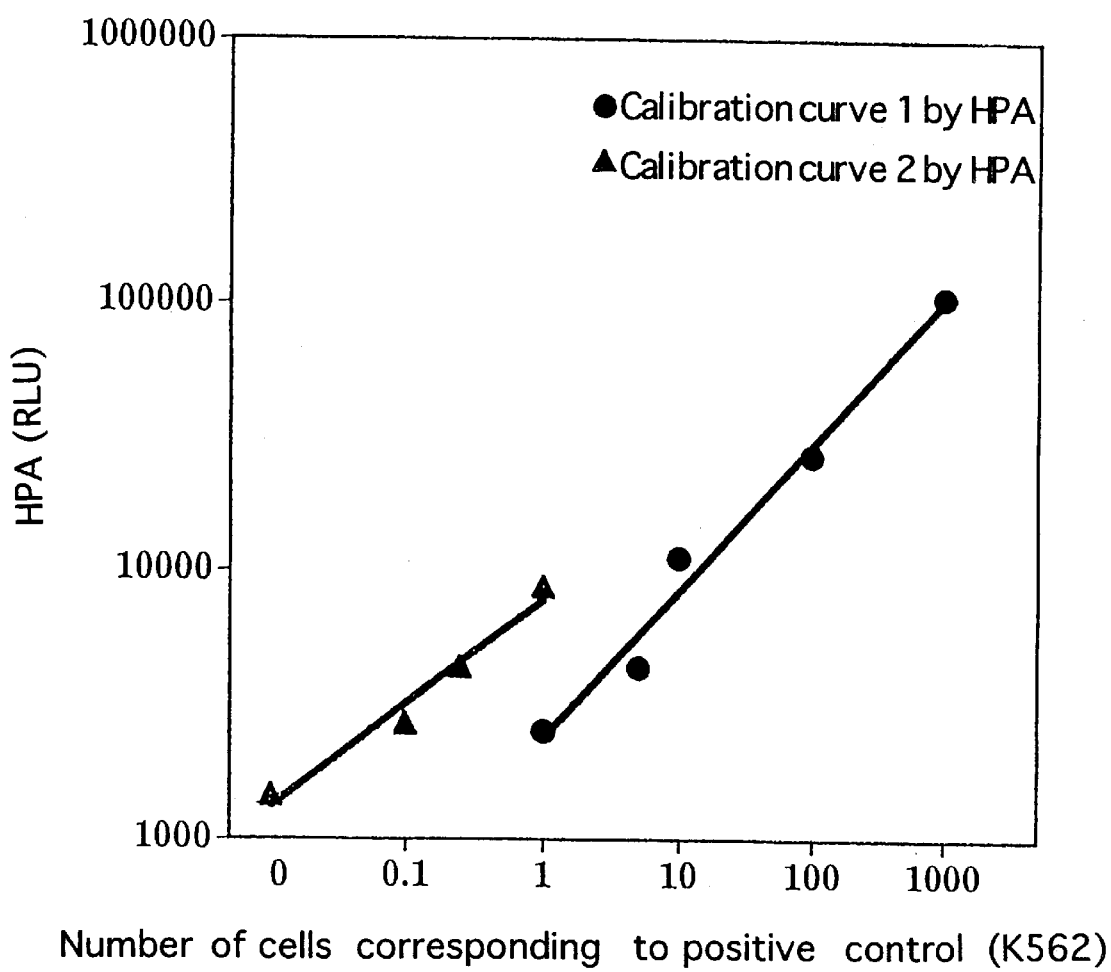
FIG. 11 is a calibration curve of telomerase activity.

As a telomerase activity positive control, stepwise dilutions of K562 cell extract were provided and TRAP was effected in a similar manner to said cancer cell lines. HPA was also done according to the method described in IV. However, to provide a wide range of linearity of the telomerase activity positive control, the amounts of the AE labelle d probe and chemiluminescence were adjusted to yield two calibration curves (FIG. 11).

From the calibration curves, the standard control number of cancer cells contained in samples was calculated. Thus, based on the HPA data obtained, the number of each cancer cell contained in a sample which corresponded to the number of positive K562 cells was calculated from the calibration curves.

The resulting value was multiplied with 0.1 to give HPA unit.

V. Results

Figure 12:
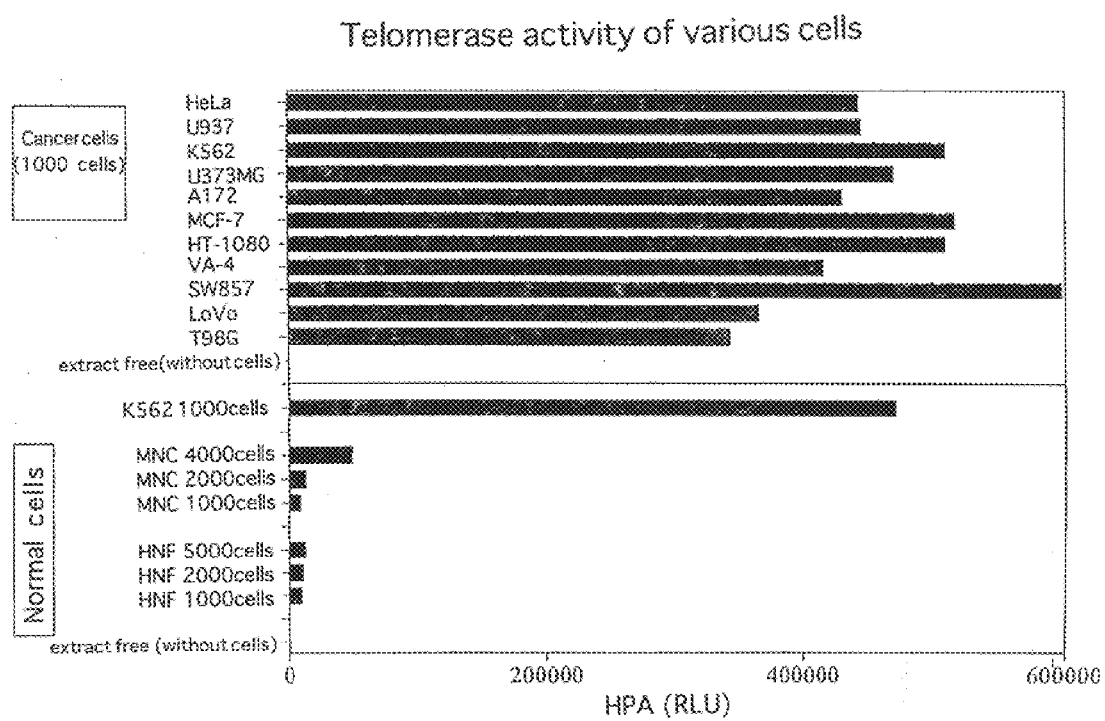
FIG. 12 shows telomerase activity of various cancer cells.

As shown in FIG. 12, various cancer cells had significant telomerase activity as compared with normal cells.

Figure 13:
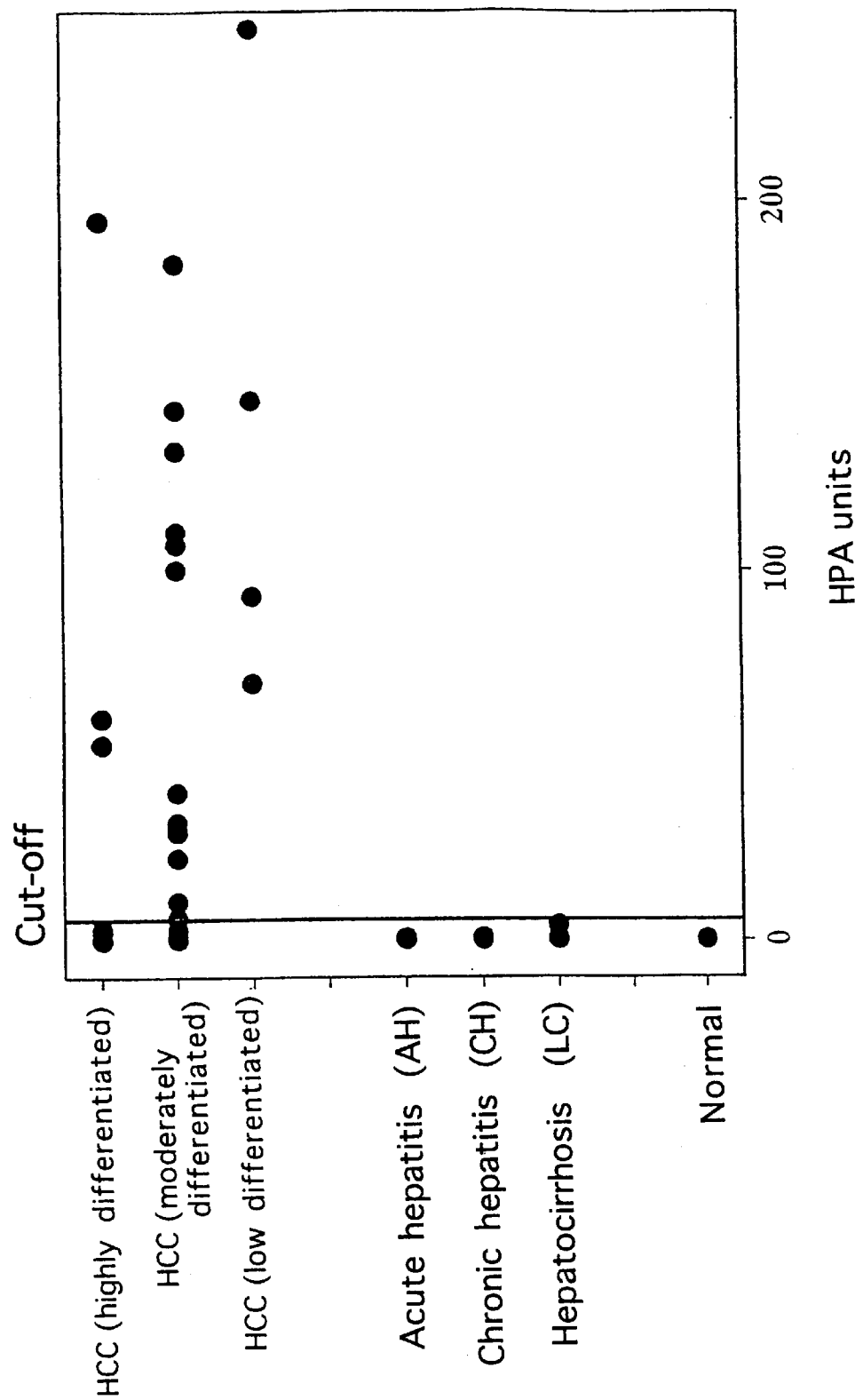
FIG. 13 shows telomerase activity of liver cancer tissues.

Further, as a result of measurement of telomerase activity for liver cancer (HCC, hepatocellular carcinoma) issues, significant telomerase activity was observed as compared with acute hepatitis, chronic hepatitis and hepatocirrhosis, irrespective of highly, moderately and low differentiated HCC, as shown in Table 1 and FIG. 13. Similar results were obtained with large intestine cancer.

TABLE 1

Telomerase activity of liver tissue

| Tissue | | Telomerase activity[a] (HPA Units[b]) | | | | Telomerase positive | |
|---|---|---|---|---|---|---|---|
| | | <0.21[c] | 0.21–10 | 10–100 | 100< | Sub-total | Total |
| HCC6 | High | 2 | 2 | 2 | 1 | 5/7 | 30/33 |
| | Moderate | 1 | 7 | 9 | 5 | 21/22 | (90.9%) |
| | Low | 0 | 0 | 2 | 2 | 4/4 | |
| Normal | | 4 | 0 | 0 | 0 | 0/4 | 0/4(0%) |
| Liver | Acute | 3 | 4 | 0 | 0 | 4/7 | 17/46 |
| Disease | Chronic | 22 | 9 | 0 | 0 | 9/31 | (37.0%) |
| | Hepato-cirrhosis | 4 | 4 | 0 | 0 | 4/8 | | a) 6 μg extract was used for each telomerase
b) relative activity of telomerase as compared with telomerase positive standard (K562 cell)
c) cut-off value (mean of normal tissues, units +2SD The method of the present invention is also effective in the diagnosis of cancer by detecting or quantitatively determining telomerase activity derived from cells contained in a specimen obtained non-invasively or invasively. The examples of cancers to be diagnosed and corresponding specimens therefor (in bracket) may include urinary bladder cancer (urine, urinary bladder wash, tissues obtained by an endoscope or operation), prostate gland cancer (prostate gland juice, tissues obtained by needle biopsy or operation), uterocervix cancer (smear, tissues obtained by an endoscope or operation), uterus cancer (tissues obtained by an endoscope or operation), breast cancer (tissues obtained by needle biopsy or operation), pancreatic cancer (pancreatic juice, duodenum juice, tissues obtained by operation), liver cancer (tissues obtained by needle biopsy or operation), oral cavity cancer (oral cavity wash, tissues obtained by operation), esophagus cancer (tissues obtained by an endoscope or operation), large intestine cancer (feces, enteron wash, tissues obtained by an endoscope or operation), gastric cancer (tissues obtained by an endoscope or operation), lung cancer (sputum, tissues obtained by an endoscope or operation), and brain tumor (tissues obtained by operation). Further, if telomerase activity is found in eucaryotic cells in peripheral blood, the method of the present invention can be utilized for the diagnosis of leukemia; if said peripheral blood is derived from a patient with a solid tumor, metastasis may be presumed.

An example of specimen which is non-invasively obtained and may be used to diagnose cancer is urine. Methods for obtaining a sample from urine may be, for example, the method described in Journal of National Institute, Vol. 89, No. 10, p.724–730, May 2, 1997 or the method described in International Journal of Oncology, 9: 1169–1173, 1996, American Cancer Society (1997) p.362–369. The urine obtained by these methods is measured for telomerase activity using the method of the present invention, whereby diagnosis of urinary bladder cancer, prostate gland cancer and kidney cancer may be possible.

As stated, the method of the present invention is very useful for the diagnosis of cancers.

Industrial Applicability:

According to the present invention, there are provided a method for the detection of telomerase activity, a method for the detection of cancer cells, a method for the diagnosis of cancers, and a kit for the detection of cancer cells and/or for the diagnosis of cancers. The present invention is useful for the diagnosis of cancers in that telomerase activity can be detected rapidly with a high sensitivity.

What is claimed is:

1. A method of detecting telomerase activity which comprises the steps of:
   (a) amplifying an extended telomeric repeat sequence using a tag-sequence reverse primer (TSRP), or a combination of primer 1 and said TSRP, wherein said TSRP comprises a tag sequence and primer 2,
   wherein said primer 1 comprises at least a nucleotide sequence represented by "AGNGTT" wherein N is A, T, G, or C, at the 3' end in thereof,
   wherein said TSRP is selected from the group consisting of SEQ ID No:22, 23, 24, 25, 26, 27 and 28 wherein primer 2 in the TSRP comprises a tag sequence having a sequence which does not hybridize with the sequence represented by "TTAGGG" and is linked to the 5' end of said primer 2, and
   (b) hybridizing the resulting amplified product with a probe labeled with a nonradioactive labeling material to detect the telomerase activity.

2. A diagnostic kit for carrying out the method of detecting telomerase activity diagnosing cancer of claim 1, said kit comprising
   (a) primer 1 which comprises at least a base sequence represented by "AGNGTT" wherein N is A, T, G, or C, at the 3' end in said primer 1;
   (b) TSRP which is selected from the group consisting of SEQ ID NO: 22–28, wherein primer 2 in the TSRP comprises a tag sequence having a sequence which does not hybridize with the sequence represented by "TTAGGG" and is linked to the 5' end of said primer 2;
   (c) a probe labeled with a non-radioactive labeling substance.

3. A method of diagnosing cancer comprising detecting cancer cells by a method of detecting telomerase activity of the cancer cells, said method comprising:
   (a) amplifying an extended telomeric repeat sequence using a tag-sequence reverse primer (TSRP), or a combination of primer 1 and said TSRP, wherein said TSRP comprises a tag sequence and primer 2;
   wherein said primer 1 comprises at least a nucleotide sequence represented by "AGNGTT" wherein N is A, T, G, or C, at the 3' end in thereof,
   wherein said TSRP is selected from the group consisting of SEQ ID NO: 22, 23, 24, 25, 26, 27 and 28 wherein primer 2 in the TSRP comprises a tag sequence having a sequence which does not hybridize with the sequence represented by "TTAGGG" and is linked to the 5' end of said primer 2,
   (b) hybridizing the resulting amplified product with a probe labeled with a nonradioactive labeling material to detect the telomerase activity.

* * * * *

SEQUENCE LISTING

<160> NUMBER OF SEQ ID NOS: 29

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: TS Primer

<400> SEQUENCE: 1
aatccgtcga gcagagtt                                          18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: CX Primer

<400> SEQUENCE: 2
cccttaccct tacccttacc ctaa                                   24

```
<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA with modified base at position 14 and 15,
      acridinium ester

<400> SEQUENCE: 3
cccttaccct aaccctaact ctgctcgac                                29

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA, with modified base at position 15 to 16,
      acridinium ester

<400> SEQUENCE: 4
cccttaccct aaccctaact ctgctcgac                                29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA with modified base at position 9 to 10, acridinium
      ester

<400> SEQUENCE: 5
accctaaccc taactctgct cgacggatt                                29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA with modified base at position 10 to 11,
      acridinium ester

<400> SEQUENCE: 6
accctaaccc taactctgct cgacggatt                                29

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA with modified base at position 13 to 14,
      acridinium ester

<400> SEQUENCE: 7
cctaacccta accctaaccc taacc                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA with modified base at position 14 to 15,
      acridinium ester
```

<400> SEQUENCE: 8
cctaacccta accctaaccc taacc                                     25

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA with modified base at position 15 to 16,
      acridinium ester

<400> SEQUENCE: 9
accctaaccc taaccctaac cctaaccct                                 29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA with modified base at position 16 to 17,
      acridinium ester

<400> SEQUENCE: 10
accctaaccc taaccctaac cctaaccct                                 29

<210> SEQ ID NO 11
<211> LENGTH: 53
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
aatttaatac gactcactat agggagactc tctctctctc tctctctaga gtt      53

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
aatccgtcga gcagagttag ggttagggtt aggg                           34

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
aatttaatac gactcactat agggaga                                   27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gaaatttaat acgactcact atagggaga                              29

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gtccctaaat taatacgact cactataggg agata                       35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
gccgggaatt taatacgact cactataggg agacc                       35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
acttcgaaat taatacgact cactataggg agacc                       35

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ggctcgaaat taatacgact cactataggg agaac                       35

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
gcgtaggaaa taatacgact cactataggg agagg                       35

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 20
attaaccctc actaaaggga ac                                          22

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
ttacccttac ccttaccct                                              19

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
acgtagcgtt agttaccctt acccttaccc t                                31

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
cgtagcgtta gttaccctta cccttaccct                                  30

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gtagcgttag ttaccttac ccttaccct                                    29

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
tagcgttagt taccttacc cttaccct                                     28

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
```

```
agcgttagtt acccttaccc ttaccct                                    27

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
gcgttagtta cccttaccct taccct                                     26

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
cgttagttac ccttaccctt accct                                      25

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA with modified base at position 14 to 15,
      acridinium ester

<400> SEQUENCE: 29
ctaaccctaa ccctaaccct aaccctaact ct                              32
```